(12) United States Patent
Matsui et al.

(10) Patent No.: US 6,174,543 B1
(45) Date of Patent: Jan. 16, 2001

(54) ANTIDIABETIC EXTERNAL SKIN APPLICATION COMPOSITION

(75) Inventors: Rakan Matsui; Yuko Kiyota; Masaya Nakashima; Toshiji Kanayama, all of Yokohama (JP)

(73) Assignee: Shiseido Company, Ltd., Tokyo (JP)

( * ) Notice: Under 35 U.S.C. 154(b), the term of this patent shall be extended for 0 days.

(21) Appl. No.: 09/362,733

(22) Filed: Jul. 29, 1999

(30) Foreign Application Priority Data

Jul. 29, 1998 (JP) .................................................. 10-228725
Jun. 30, 1999 (JP) .................................................. 11-184828

(51) Int. Cl.[7] .............................. A61K 9/70; A61F 13/00; C07C 303/00
(52) U.S. Cl. ...................... 424/443; 424/449; 424/447; 564/41
(58) Field of Search .................................. 424/443, 447, 424/449

(56) References Cited

U.S. PATENT DOCUMENTS

| 4,801,458 | 1/1989 | Hidaka et al. | 424/443 |
|---|---|---|---|
| 5,258,185 | 11/1993 | Bauer et al. | 424/484 |
| 5,446,070 | * 8/1995 | Mantelle | 514/772.6 |
| 5,455,042 | * 10/1995 | Sakai et al. | 424/443 |

FOREIGN PATENT DOCUMENTS

| 2173366 | 4/1995 | (CA) . |
| 43 36 159 | 10/1993 | (DE) . |
| 3-86825 | 4/1991 | (JP) . |
| 4-18023 | 1/1992 | (JP) . |

OTHER PUBLICATIONS

Bander et al. "Zur Pharmakologie von HB 419, enem neuen, start wirksmen oralen Antifiabeticum", Arzneim Forsch, vol. 19(8a), pp. 1363–1368, 1969.

K. Schoffling, "Stand der Therapie mit Sulfonylharnstoffen und Biguaniden", Therapiewoche, vol. 18, pp. 11–20 1968.

Gekkan Yakuji (Japanese), vol. 31, No. 4, pp.663–667 (1989).

T. Yamamoto et al., "Topical application of the hypoglycemic agent glibenclamide and changes in blood glucose, plasma insulin (IRI) levels and plasma concentration of glibenclamide in normal rats", Diabetes Resrch. & Clinical Practice, 8, pp. 19–22 (1990).

N.M. Sanghavi et al., "Solubilization of Glibenclamide with B–Cycodextrin G its Derivatives", Drug Dev. & Indus. Pharm. 20(7), pp. 1275–1283.

Takahashi et al., "Trial for Transdermal Administration of Sulfonylureas", Yakugaku Zasshi, 117 (12), pp. 1022–1027 1997.

El–Massik et al, "Development of a dissolution medium for glibenclamide", Inter'l J. of Pharm. 140, pp.69–76.

* cited by examiner

Primary Examiner—Thurman K. Page
Assistant Examiner—P. E. McQueeney
(74) Attorney, Agent, or Firm—Foley & Lardner

(57) ABSTRACT

An antidiabetic external skin application composition containing glibenclamide and benzyl alcohol and optionally a nonionic surfactant.

13 Claims, 2 Drawing Sheets

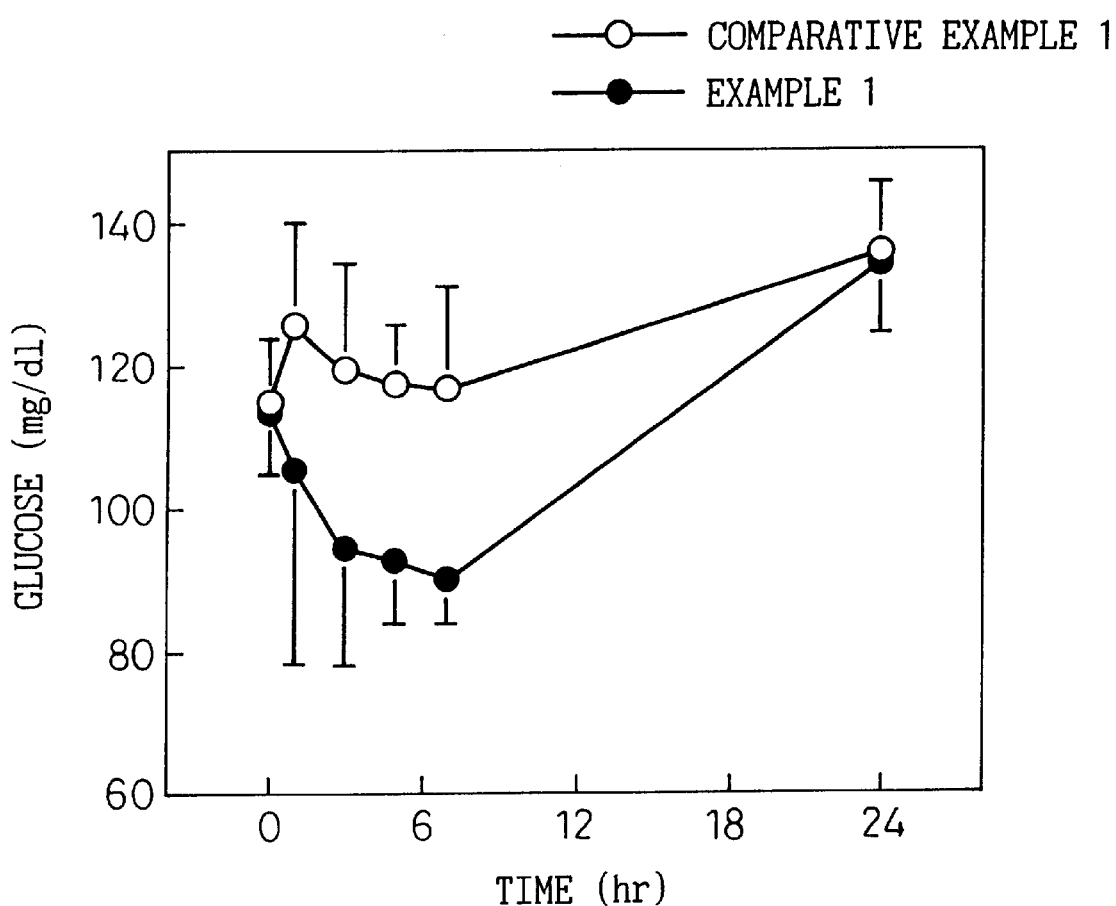

ANTIDIABETIC EXTERNAL SKIN APPLICATION COMPOSITION

BACKGROUND OF THE INVENTION

1. Field of the Invention

The present invention relates to an antidiabetic external skin application composition and, more specifically relates to an antidiabetic external skin application composition containing glibenclamide formulated therein.

2. Description of the Related Art

Glibenclamide is a sulfonylurea type oral hypoglycemic drug developed by cooperative study of Boehringer Mannheim and Hoechst in 1966 and is now commercially available in the field of drugs in the form of tablets (Trade name: Euglucon tablet available from Yamanouchi Seiyaku K. K., Japan, Trade name: Daonil available from Japan Hoechst). Such tablets containing, as an effective ingredient, glibenclamide formulated therein are conventionally used because they provide a strong hypoglycemic action at a small dosage, as described in, for example, Arzneim Forsch, vol. 19(8a), 1363–1368 (1969); Therapiewoche, vol. 18, 11–20 (1968).

Nevertheless, the tablet containing, as an effective ingredient, glibenclamide formulated therein is a powerful drug, as described in, for example, the attached statement of the powers of Euglucon tablet (Yamanouchi Seiyaku K. K.) that, since the tablet sometimes causes, as a side effect, a significant and prolonged hypoglycemia, the dosage regimen should be specially attentioned. Furthermore, since numbers of diabetes mellitus of aged people are recently increasing, as pointed out in, for example, Gekkan Yakuji (Japanese), Vol. 31, No. 4, 663–667 (1989), the dosage is especially important in the administration of the oral hypoglycemic drug to aged people.

In order to reduce the danger of the side effect as mentioned above, it is convenient that, if the tablet can be made in the form of a percutaneously absorbable external skin treatment agent (or ointment), the application amount can be easily adjusted and, in addition, even if rapid hypoglycemic action occurs, the agent can be easily washed out, for example, and therefore, the danger can be avoided. As the form of drug other than the oral administration type tablets, the application type external skin treatment agent (e.g., ointment) is known in the art (e.g., JP-A-4-18023, JP-A-3-86828). However, because of the characteristics of glibenclamide mentioned below, the prior application type external skin treatment agents have not been satisfied from the viewpoints of stability and percutaneous absorbability.

Namely, since glibenclamide is not soluble in most of solvents, it is very difficult to prepare the external skin treatment type agent thereof. Furthermore, although it is known in the art that glibenclamide is soluble in dimethylsulfoxide, it is not usable in the form of the dimethylsulfoxide solution from the viewpoint of safety. Thus, although the external skin, application type agent is desired, it has not been yet developed from the practical point of view.

SUMMARY OF THE INVENTION

Accordingly, the objects of the present invention are to eliminate the above-mentioned problems of the prior art and to provide an antidiabetic external skin application composition capable of containing the effective ingredient, glibenclamide, formulated in the dissolved form and having excellent percutaneous absorption and stability.

The present inventors have found, as a result of the extensive study, that benzyl alcohol has an excellent solubility for glibenclamide and both benzyl alcohol and glibenclamide can be formulated to obtain the desired antidiabetic external skin application composition. The stability and the solubility are generally inconsistent with each other and, when the solubility is increased, the stability generally or often is decreased. However, benzyl alcohol has especially excellent solving power for glibenclamide, among the other various solvents, and provides good stability when compared with the use of the other solvents. Thus, the present invention has been completed based upon these findings.

In accordance with the present invention, there is provided an antidiabetic external skin application composition comprising glibenclamide and benzyl alcohol.

In the present invention, the composition is most stable when the pH thereof is within the range of 8–10 and preferably contains a nonionic surfactant to improve the stability.

BRIEF DESCRIPTION OF THE DRAWINGS

The present invention will be better understood from the description set forth below with reference to the accompanying drawings, wherein:

FIG. 3 is a drawing exhibiting the hypoglycemic action of one example of the antidiabetic external skin application composition according to the present invention.

DESCRIPTION OF THE PREFERRED EMBODIMENTS

Figure 1:
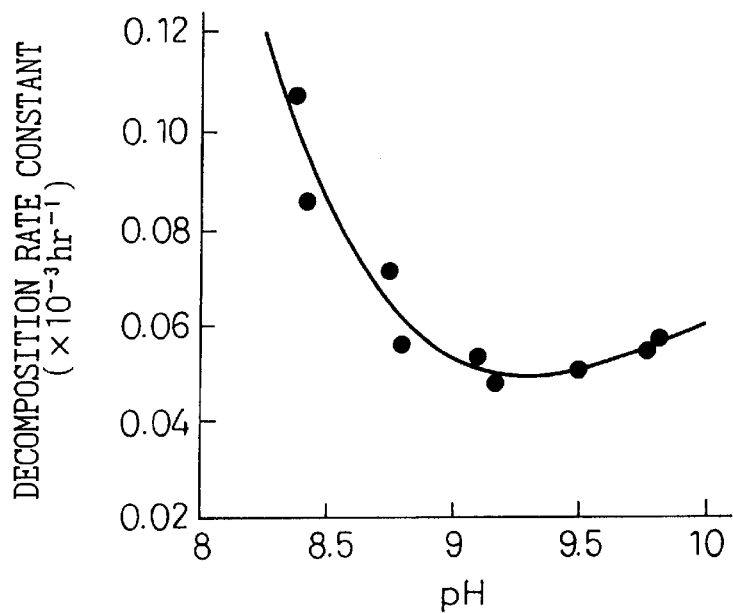
FIG. 1 is a drawing illustrating the pH dependency of the decomposition rate constant of glibenclamide in the preparation containing glibenclamide formulated therein.

As the form of the antidiabetic external skin application composition according to the present invention, coating type or application type is exemplified. Among these, examples of the coating type external skin application composition are lotion, jelly, cream, milky lotion, ointment, etc. Examples of the application type external skin application composition are plaster, cataplasm, patch preparation, etc.

The glibenclamide usable in the present invention is widely known in the art as an antidiabetic agent, as mentioned above and is formulated in the external skin application composition in an amount of, preferably 0.5 to 3.0% by weight, more preferably 1.0 to 2.0% by weight, based upon the total weight of the composition. When the amount of glibenclamide formulated is too large, the stability of the preparation composition tend to be decreased.

The amount of benzyl alcohol formulated in the present composition is preferably 1.0% by weight or more, based upon the total amount of the composition. When the amount of benzyl alcohol is less than 1.0% by weight, the solubility of the glibenclamide tends to become insufficient.

The antidiabetic external skin application composition according to the present invention preferably contains water and has a pH of, preferably 8–10, more preferably 9–9.5, for the purpose of improving the thermal stability. Furthermore, when a basic substance such as triethanolamine, triisopropanolamine, etc. is formulated into the present composition, the solubility of the glibenclamide is further improved.

In the present invention, the stability can be improved by the use of a nonionic surfactant. Examples of such nonionic surfactant are polyoxyethylene sorbitan fatty acid esters, sorbitan fatty acid esters, polyoxyethylene hydrogenated castor oils, polyethyleneglycol fatty acid esters, polyoxyethylene alkyl ether, polyoxyethylene glycerol fatty acid esters, glycerol fatty acid esters, polyoxyethylene alkylphenyl ethers, etc. These nonionic surfactants may be used alone or in any mixture thereof. Among these surfactants, the use of polyoxyethylene sorbitan fatty acid esters is preferable, because white turbidity does not occur at a low temperature and the stability is further improved.

The preferable amount of the nonionic surfactant formulated in the skin external application composition of the present invention is preferably 1.0 to 5.0% by weight, more preferably 2.0 to 3.0% by weight, based upon the total amount of the composition.

The antidiabetic external skin application composition according to the present invention may optionally contain other known components for drug compositions, as long as the objects of the present invention can be accomplished. Examples of such components are hydrocarbons such as liquid paraffin, squalane, vaseline; oil and fats such as Macadamia nut oil, lanolin; waxes such as jojova oil, carnauba wax, candelilla wax; silicones such as dimethyl polysiloxane, methylphenyl siloxane; higher alcohols such as capryl alcohol, lauryl alcohol, myristyl alcohol, cetyl alcohol, cholesterol; higher fatty acids such as capric acid, myristic acid, palmitic acid, stearic acid, behenic acid, linoleic acid; humectants such as polyethylene glycol, propylene glycol, dipropylene glycol, glycerol, 1,3-butylene glycol, xylitol, sorbitol, multitol, chondroitin sulfuric acid, hyaluronic acid, mucoitin sulfuric acid, caronic acid, atherocollagen, cholesteryl-12-hydroxystearate, sodium lactate, bile acid esters, dl-pyrrolidone carboxylic acid salts, short-chain soluble collagen, diglycerol (EO) PO addition products, rosa roxburghii extracts, achillea milleifolium extracts, meliloti herba extracts; lower alcohols such as ethanol; antioxidants such as butylhydroxy toluene, tocopherol, ficin; antibiotic agent such as benzoic acid, salicylic acid, sorbic acid, p-oxybenzoic acid alkyl esters, hexachlorophene; amino acids such as glycine, alanine, valine, leucine, threonine, phenylalanine, tyrosine, aspartic acid, asparagine, glutamine, taurine, arginine, histidine, and alkali metal salts and hydrochlorides thereof; organic acids such as glutathione, citric acid, malic acid, tartaric acid, lactic acid; vitamins such as, for example, vitamin A and the derivatives thereof, vitamin Bs such as vitamin B6 hydrochloride, vitamin B6 tripalmitate, vitamin B12, vitamin C such as ascorbic acid, ascorbic acid sulfate esters (salts), ascorbic acid dipalmitate, vitamin Es such as α-tocopherol, β-tocopherol, vitamin E acetate, vitamin Ds, vitamin H, pantothenic acid, pantethine; various drugs or agents such as nicotinic amide, allantoin, glycyrrhizic acid (salt), glycyrrhetic acid, hinokitiol, bisabold, eucalyptone, thymol, inositol, saponins such as bupleurum root saponin, ginseng saponin, luffa cylindrica saponin, pantothenyl ethyl ether, tranexamic acid, arbutin, cepharanthine, placental extracts; natural extracts, with organic solvents, alcohols, polyols, water, aqueous alcohol, of rumex crispus, saphora flavescens, nuphar japonicum, orange, salvia officinalis, achillea alpina, malva sylvestris, swertia japonica, hondoensis, equisetum arvens, luffa cylindrica, aesculus hippocastanum, arnica montana, lily, artemisia princeps, paeonia lactiflora, aloe, gardenia jasminoides, chamaecyparis pisifera; cationic surfactants such as stearyl trimethylammonium chloride, benzalkonium chloride, laurylamine oxide; anionic surfactants such as sodium palmitate, sodium laurate, potassium laurate, sodium laurylsulfate, triethanolamine alkyl sulfate, acylmethyl taurine salts; amphoteric surfactant; neutralizing agents; sequestering agent, powder components, dyes; fragrants; UV absorbents; etc.

EXAMPLES

The present invention will now be further illustrated by, but is by no means limited to, the following Examples. All the amounts in the Examples are in terms of % by weight.

(1) Measurement of Solubility

Using various solvents shown in Table 1, the solubilities of glibenclamide were determined at 25° C. The results are shown in Table 1.

TABLE 1

| Solvents | Solubilities (mg/ml) |
|---|---|
| Acetone | 6.77 |
| Isopropanol | 1.24 |
| Ethanol | 2.54 |
| Propylene carbonate | 5.64 |
| Triacetyne | 0.55 |
| Benzyl alcohol | 10.0 or more |
| Isopropyl myristate | 0.06 |
| Diisopropyl adipate | 0.57 |
| Crotamiton | 8.57 |

As is clear from Table 1, glibenclamide has good solubility in benzyl alcohol.

Example 1

| | |
|---|---|
| (1) Polyvinyl pyrrolidone | 1.0% by weight |
| (2) Sodium sulfite | 0.1 |
| (3) Glibenclamide | 0.05–2.0 |
| (4) Benzyl alcohol | 3.0 |
| (5) Triethanol amine | 3.0 |
| (6) Polyoxyethylene (20) sorbitan monooleate | 1.0 |
| (7) Ethanol | 36.0 |
| (8) Purified water | Balance |
| pH | 8.39–9.82 |

(Preparation)

The component (8) was added to the components (1) and (2) and the mixture was dissolved under mixing (i.e., aqueous phase). On the other hand, the components (3), (4) and (5) were mixed and the component (6) was dissolved therein by heating at 60° C., followed by adding the component (7) (i.e., ethanol phase). The aqueous phase and the ethanol phase are mixed to be solubilized.

(1) Stabilization Test

A lotion preparation having a glibenclamide content of 1.0% by weight in Example 1 was allowed to stand at 50° C. for one month. The retention rate of the glibenclamide was 95.9%.

(2) pH Dependency Test of Heat Stability

As the content of glibenclamide formulated is increased, the pH is decreased and the stability is decreased. Accordingly, the test samples composition were prepared according to the formulation in Example 1 and, after the samples were allowed to stand at 50° C. for one month, the decomposition rate constants of glibenclamide were determined to evaluate the pH dependency of the heat stability.

The results are shown in FIG. 1. As is clear from the results shown in FIG. 1, the pH value of 9–9.5 provide the best heat stability.

(3) In Vitro Permeation Test for Skin of Rat

For sample compositions containing glibenclamide in the contents of 0.5% by weight (i.e., 0.5% GC-1), 1.0% by weight (i.e., 1% GC-1) and 2.0% by weight (i.e., 2% GC-1) formulated in the compositions of Example 1, in vitro permeation experiment was carried out using extirpated skin of rat by the following method.

Comparative control samples having 0.5% by weight glibenclamide solution (0.5% DMFA solution) and 2.0% by weight glibenclamide solution (2% DMFA solution) were prepared in the same manner as in Example 1, except that dimethyl formamide (DMFA) was used, instead of benzyl alcohol, as a solvent and were subjected to the same experiment.

(i) Test Method

From clearly shaven abdomen of male Wistar rats (7 week age), sample skins were obtained and stored under refrigeration. When the experiment was started, the connective tissues etc. of the extirpated skin was removed with tweezers in a physiological saline and attached to a Franz type diffusion cell (permeation area=3.14 cm$^2$). In the acceptor side, about 17 ml of 50 mmol/l isotonic phosphate buffer (pH=7.4) was added and stirred with a stirrer at 37° C. On the other hand, in the donor side, 4 ml each of the above samples was added. The experiment was carried out by wrapping the upper side with paraffin. The sampling was carried out by accurately taking out 1 ml of a sample with the elapse of time. To the sample, the same amount of 50 mmol/l isotonic phosphate buffer (pH=7.4) stored at 37° C. was added. The determination was carried out until 24 hours. The quantitative determination was carried out by means of HPLC (i.e., high performance liquid chromatography).

(ii) Result

Figure 2:
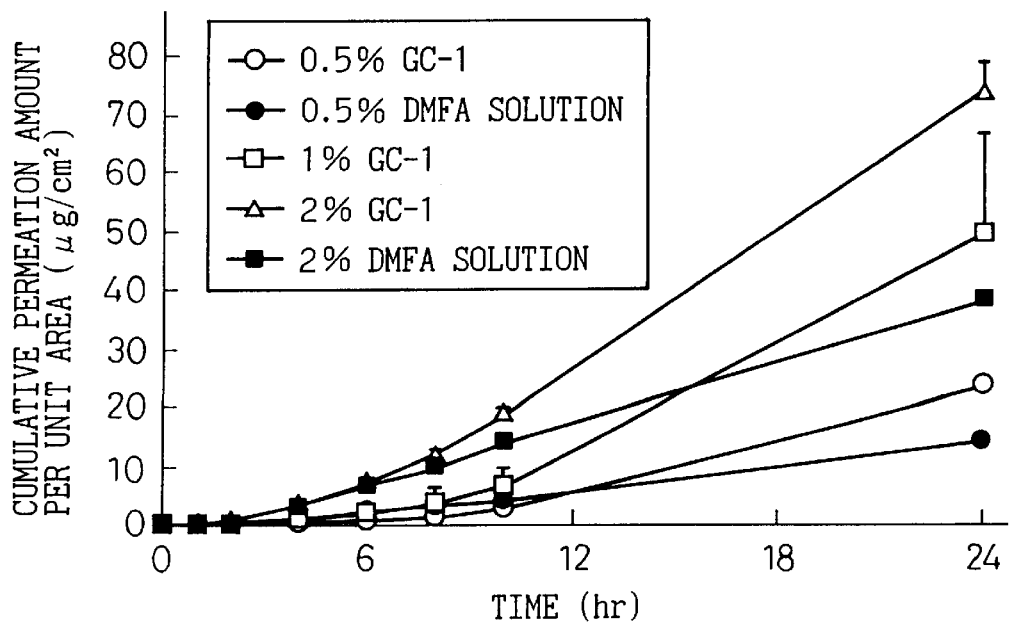
FIG. 2 is a drawing illustrating one example of the correlationship between the cumulative permeation amount and the time in the in vitro skin permeation test of the rat.

The results are shown in FIG. 2. The permeation amount through the skin from the composition is increased with the increase in the concentration of glibenclamide. Furthermore, the composition of Example 1 according to the present invention show the rapid permeation speed at the steady state, when compared with the control DMFA solution, whereas the lag time of the present compound is longer than that of the control DMFA solution. It is clear from these results that the partition of the present composition is clearly higher than that of the control DMFA solution. Thus, according to the formulation of the present invention, the partition to the skin can be improved, and therefore, the desired antidiabetic external skin application composition having a good skin permeation and excellent percutaneous absorption can be obtained.

Comparative Example 1

A lotion composition was prepared in the same manner as in Example 1 except that the glibenclamide in the lotion composition containing 1.0% by weight of glibenclamide was replaced with purified water.

The hypoglycemic actions of the lotion compositions of Example 1 (glibenclamide: 1.0% by weight) and Comparative Example 1 (no glibenclamide) were tested as follows.

(i) Test animal Male Wistar rats (7 week age, about 200 g weight)

(ii) Sample group and number of animals Example 1: 1 group×7 rats Comparative Example 1: 1 group×7 rats (iii) Procedure One day before the test, the body weight of the animal was weighed and, then, the back was shaven with hair clippers under etherization. The rat was fasted overnight. The blood sampling was carried out by taking the outflowing blood through a capillary tube after injuring (or cutting) the caudal vein. The application amount of the sample composition to be tested was 50 μl per 100 g of body weight and the sample composition was uniformly and entirely coated on the previously shaved skin of the back with a spatula. 20 μl of blood serum was collected by allowing the sample blood to stand at room temperature for 20 minutes, followed by centrifugal separation (3000 rpm, 4° C., 20 min). The blood serum thus obtained was maintained at −20° C. until the quantitative determination of the blood glucose level. The quantitative determination of the blood glucose level was carried out (sino test, sino test Co., LTD.) according to an enzymatic colorimetry.

(iv) Result

The results are shown in FIG. 3. As is clear from FIG. 3, the lotion composition of Example 1 exhibits a remarkable hypoglycemic action after 2 hours from the application, and this action arrived at the peak between 3 hours and 7 hours from the application and disappeared after 24 hours from the application. The Comparative lotion did not show the hypoglycemic action.

Example 2

| | |
|---|---|
| (1) Glibenclamide | 1.0% by weight |
| (2) Benzyl alcohol | 3.0 |
| (3) Triethanol amine | 4.0 |
| (4) Polyethylene glycol 400 | 9.0 |
| (5) Polyoxyethylene (20) Sorbitan monooleate | 2.0 |
| (6) Ethanol | 28.0 |
| (7) Carboxyvinyl polymer | 1.0 |
| (8) Sodium sulfite | 0.1 |
| (9) Purified water | Balance |

(Preparation)

The components (1), (3) and (5) were added to the component (2) and the mixture was dissolved by heating at 60° C., followed by adding thereto the components (4) and (6) followed by mixing to prepare an ethanol phase. The components (7) to (9) were dissolved by mixing to prepare an aqueous phase. Thereafter, the ethanol phase was added to the aqueous phase while stirring. After the addition, the mixture was thoroughly mixed to obtain a jelly preparation.

(1) Stability Test

The retention rate of the glibenclamide in Example 2 (i.e., 1% by weight jelly preparation) after allowing to stand at 50° C. for one month was 94.1%.

Example 3

| | |
|---|---|
| (1) Glibenclamide | 2.0% by weight |
| (2) Cetyl alcohol | 2.0 |
| (3) Stearyl alcohol | 1.0 |
| (4) Behenic acid | 1.5 |
| (5) White vaseline | 3.0 |
| (6) Liquid paraffin | 7.0 |
| (7) Benzyl alcohol | 5.0 |
| (8) Triethanol amine | 3.0 |
| (9) Polyoxyethylene hydrogenated castor oil 60 | 2.0 |
| (10) Monostearic glycerol | 3.0 |
| (11) Conc. glycerol | 3.0 |
| (12) 1,3-Butylene glycol | 5.0 |
| (13) Purified water | Balance |

(Preparation)

The components (1)–(10) were mixed and dissolved at 80° C. to obtain an oily phase. After the components (11)–(13) were dissolved by mixing, the mixture was heated to 70° C. and the oily phase was added and emulsified.

The resultant emulsion was cooled under stirring to obtain a cream preparation.

Example 4

|  |  |  |
|---|---|---|
| (1) Glibenclamide | 2.0% by weight |
| (2) Cetyl alcohol | 1.0 |
| (3) Stearic acid | 1.0 |
| (4) Hydrogenated oil | 2.0 |
| (5) Liquid paraffin | 7.0 |
| (6) Benzyl alcohol | 5.0 |
| (7) Triethanol amine | 3.0 |
| (8) Polyoxyethylene hydrogenated castor oil 60 | 2.0 |
| (9) Monostearic glycerol | 3.0 |
| (10) Conc. glycerol | 3.0 |
| (11) 1,3-Butylene glycol | 5.0 |
| (12) Carboxyvinyl polymer | 0.2 |
| (13) Purified water | Balance |

(Preparation)

The components (1)–(9) were mixed and dissolved at 80° C. to obtain an oily phase. After the components (10)–(13) were mixed and dissolved, the mixture was heated to 70° C., followed by adding thereto the oily phase to obtain an emulsion. The resultant emulsion was cooled, while stirring, to obtain a milky lotion.

Example 5

|  |  |  |
|---|---|---|
| (1) Glibenclamide | 1.0% by weight |
| (2) White vaseline | 40.0 |
| (3) Cetyl alcohol | 20.0 |
| (4) Sesquioleic sorbitan | 5.0 |
| (5) Benzyl alcohol | 3.0 |
| (6) Triethanol amine | 2.0 |
| (7) Purified water | Balance |

(Preparation)

The components (1)–(6) were mixed and dissolved at 80° C., followed by adding thereto and mixing therewith the component (7). The mixture was cooled while stirring to obtain an ointment.

Example 6

|  |  |  |
|---|---|---|
| (1) Glibenclamide | 2.0 g |
| (2) Benzyl alcohol | 5.0 |
| (3) Triethanol amine | 3.0 |
| (4) Polyoxyethylene (20) sorbitan monooleate | 1.0 |
| (5) Acrylic polymer | 15.0 |
| (6) Triethyl acetate | 11.0 |
| (7) Acetone | 160.0 |
| (8) Citric acid | 0.3 |
| (9) Purified water | q.s. |

An aqueous phase obtained by dissolving the component (8) in the component (9) was mixed with an organic phase obtained by dissolving the components (1)–(7) under mixing. The mixture was developed on a non-woven fabric such that the glibenclamide was coated at a coverage of 1 mg/cm$^2$, followed by drying at 60° C. for 2 hours. Thus, a patch preparation was obtained.

As explained above, the antidiabetic external skin application composition can effectively lower the blood glucose level in the body by coating or applying the same to the skin and also exhibit the excellent stability. Since the antidiabetic external skin application composition according to the present invention is in the form of coating or applying to the skin, the amount of the application can be easily adjusted and, even if the blood glucose level is too decreased, the further permeation into the body can be easily prevented by immediately wiping off or washing out the coated portion, or peeling off the preparation.

What is claimed is:

1. An antidiabetic external skin application composition comprising glibenclamide, benzyl alcohol and a nonionic surfactant in an amount sufficient to increase glibenclamide retention compared to a composition that lacks a nonionic surfactant.

2. An antidiabetic external skin application composition as claimed in claim 1, wherein the amount of the benzyl alcohol formulated in the composition is 10% by weight or more, based upon the weight of the glibenclamide.

3. An antidiabetic external skin application composition as claimed in claim 1, wherein the pH range of the composition is 8 to 10.

4. An antidiabetic external skin application composition as claimed in claim 1, wherein the nonionic surfactant is a polyoxyethylene sorbitan fatty acid ester.

5. An antidiabetic external skin application composition as claimed in claim 1, wherein the external skin application composition is in the coating type form.

6. An antidiabetic external skin application composition as claimed in claim 1, wherein the external skin application composition is in the application type form.

7. An antidiabetic external skin application composition as claimed in claim 2, wherein the pH range of the composition is 8 to 10.

8. An antidiabetic external skin application composition as claimed in claim 2, wherein the external skin application composition is in the coating type form.

9. An antidiabetic external skin application composition as claimed in claim 3, wherein the external skin application composition is in the coating type form.

10. An antidiabetic external skin application composition as claimed in claim 4, wherein the external skin application composition is in the coating type form.

11. An antidiabetic external skin application composition as claimed in claim 2, wherein the external skin application composition is in the application type form.

12. An antidiabetic external skin application composition as claimed in claim 3, wherein the external skin application composition is in the application type form.

13. An antidiabetic external skin application composition as claimed in claim 4, wherein the external skin application composition is in the application type form.

* * * * *